United States Patent [19]

Gounder et al.

[11] 4,366,302
[45] Dec. 28, 1982

[54] IMIDE-ANHYDRIDES AND EPOXY RESIN SYSTEMS CONTAINING SUCH COMPOUNDS

[75] Inventors: Raj N. Gounder, Robbinsville, N.J.; John T. Geary, Erie, Pa.

[73] Assignee: Lord Corporation, Erie, Pa.

[21] Appl. No.: 273,808

[22] Filed: Jun. 15, 1981

[51] Int. Cl.³ ............... C08G 59/42; C08G 59/44
[52] U.S. Cl. ................... 528/99; 525/504; 528/96; 528/114; 528/117; 528/322; 528/361
[58] Field of Search ............ 528/96, 114, 117, 99, 528/322, 361; 525/504

[56] References Cited

U.S. PATENT DOCUMENTS

| | | | |
|---|---|---|---|
| 3,346,665 | 10/1967 | Schwarzer | 528/117 X |
| 4,113,737 | 9/1978 | Balme et al. | 260/326.26 |
| 4,273,916 | 6/1981 | Jones | 528/117 |

Primary Examiner—Earl A. Nielsen
Attorney, Agent, or Firm—John A. Gazewood

[57] ABSTRACT

Imide-anhydrides having the structure

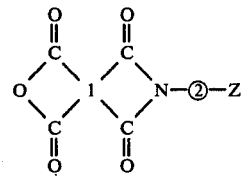

wherein ①  and ② are certain cycloaliphatic or aromatic groups and Z is selected from certain imide-anhydride and other substituents have been found to provide cured epoxy resin systems characterized by high temperature stability and excellent mechanical and physical properties.

10 Claims, No Drawings

IMIDE-ANHYDRIDES AND EPOXY RESIN SYSTEMS CONTAINING SUCH COMPOUNDS

BACKGROUND OF THE INVENTION

1. Field of the Invention

This invention relates to epoxy resin compositions. More particularly, the invention relates to epoxy resin compositions which are curable at ambient temperatures to afford products having useful properties at high temperatures.

2. Description of the Prior Art

Epoxy resins are among the most versatile of the plastic materials. Because of their toughness, adhesion, chemical resistance and electrical properties, the combination of which is not found in any other single organic polymeric material, the epoxy resins are widely used in coating, adhesives, casting, molding, laminating, potting and encapsulation, and reinforced plastic applications. In general, the epoxy resin is not used by itself but requires the addition of a curing agent or hardener to convert the resin to a crosslinked material. Curing agents which are commonly employed with epoxy resins include aliphatic and aromatic amines, polyamides, tertiary amines, amine adducts, acids, acid monoanhydrides, acid dianhydrides, aldehyde condensation products, and Lewis acid type catalysts. Selection of an appropriate curing agent depends upon system requirements such as mixture viscosity, system mass and temperature, and the characteristics desired in the cured resin such as resistance to temperature and chemicals, electrical properties, and the like.

In recent years, there has been an increasing demand from the aerospace industry and other industrial applications for materials having high-temperature utility. High-temperature utility can be improved through the use of anhydride and certain amine curing agents at elevated curing cycles, as well as through the use of epoxy resins obtained by the epoxidation, with peroxy compounds, of double bonds in certain Diels-Alder adducts. However, in many applications the high-temperature utility is insufficient. Studies indicate that temperature resistance, as well as chemical and heat resistance, is a function of crosslink density of the cured resin, with higher crosslink density affording improvements in these properties. Higher crosslink density can be achieved by increasing the functionality of either the epoxy resin or the hardening agent.

Organic acid dianhydrides which contain other cyclic or aromatic structures and have high functionality have been found to impart improved high temperature resistance as well as increased chemical and solvent resistance, to cured epoxy resin compositions. Illustrative of such acid dianhydrides are pyromellitic dianhydride, cyclopentadiene dianhydride, and benzophenone tetracarboxylic dianhydrides. Unfortunately, these organic acid dianhydrides suffer from the drawback that they are generally high melting solids which are not soluble to any appreciable extent in common solvents or epoxy resins and therefore are difficult to incorporate in epoxy resins except at elevated temperatures. In addition, epoxy resin compositions containing these organic acid dianhydrides as curing agents require high temperature curing cycles.

Thus, there is a continuing search for new epoxy resins and curing agents which can be cured at low temperatures to afford cured resin systems having good high temperature stability.

BRIEF SUMMARY OF THE INVENTION

In accordance with the present invention, it has been found that certain imide anhydride curing agents can be readily incorporated into epoxy resins to afford epoxy compositions curable at room temperature to provide cured epoxy systems characterized by high temperature stability and excellent mechanical and physical properties. Because the epoxy resin compositions of the invention are curable at room temperature, the compositions of the invention are advantageously provided as a two-pack epoxy resin system comprising:

(a) a first pack comprising an imide anhydride having the structure

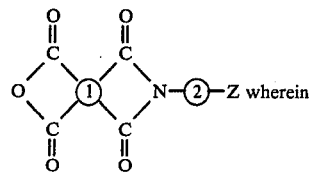 wherein

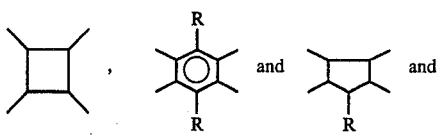

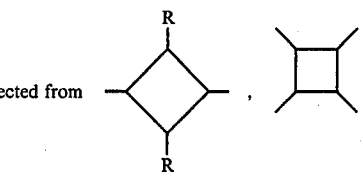

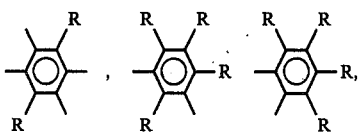

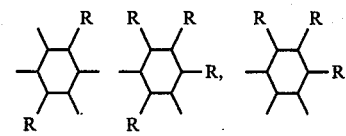

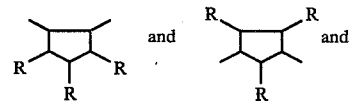

Z is selected from 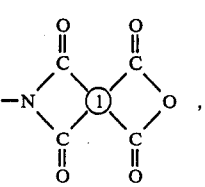

-continued

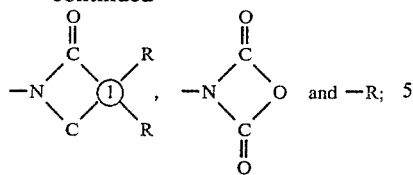

wherein $R^2$ is selected from the group consisting of hydrogen, halogen, alkyl group having from 1 to 4 carbon atoms, hydroxyl, carboxyl and amine; with the proviso that, in all cases, either

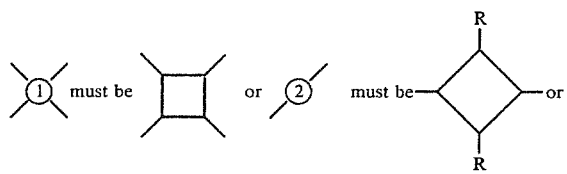

is selected from the group consisting of

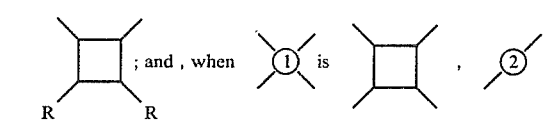

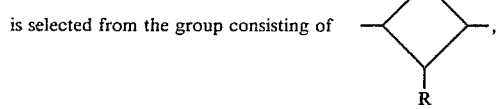

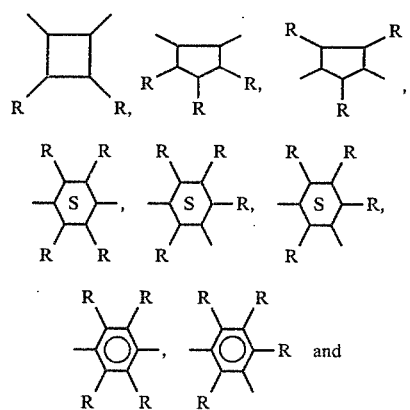

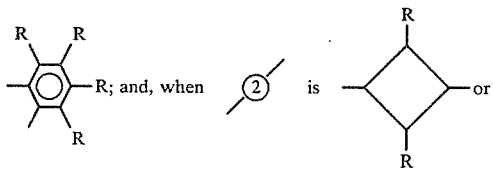

is selected from the group consisting of

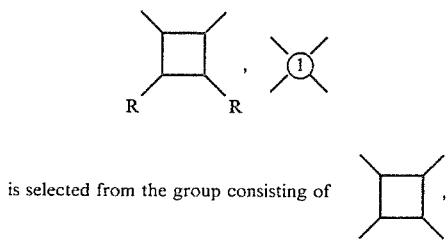

-continued

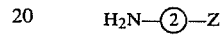

(b) a second pack comprising an epoxy resin substantially free of active hydrogen having a 1,2 epoxy equivalent value of greater than 1 and capable of solubilizing said imide anhydride.

DETAILED DESCRIPTION OF THE INVENTION

The imide anhydrides which are employed in the practice of the present invention are normally solid compounds prepared by reacting a cycloaliphatic or aromatic amine having the structure:

$$H_2N-②-Z$$

wherein —②— and Z are as defined above, with a cycloaliphatic or aromatic tetracarboxylic acid dianhydride having the structure:

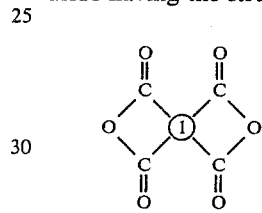

(hereinafter referred to as "dianhydride") wherein ① is as defined above. The reaction of the dianhydride and amine to provide the imide anhydride curing agents can be carried out by first adding a solution of the dianhydride to a solution of the amine to form the corresponding hydroxamic acid. This reaction to the hydroxamic acid proceeds readily at room temperature but elevated temperatures can be employed to hasten the reaction, if desired. The resulting hydroxamic acid is then condensed to the desired imide anhydride by simply heating the hydroxamic acid to an elevated temperature, for instance, above 180° C. Alternatively, the conversion to the imide anhydride can be effected at lower temperatures by the use of appropriate solvents, for example, a mixture of pyridine and acetic anhydride pursuant to condensation methods and techniques well-known in the art.

The imide anhydrides of the invention fall into one of the following four classes of compounds:

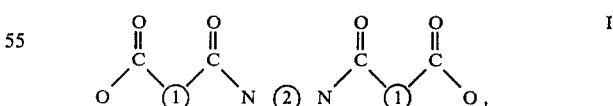 I

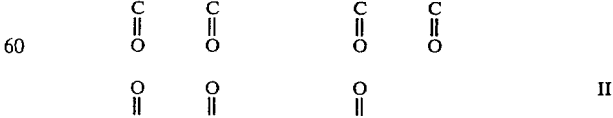 II

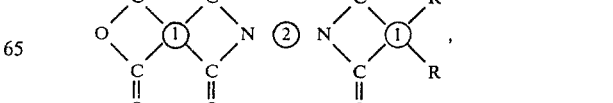

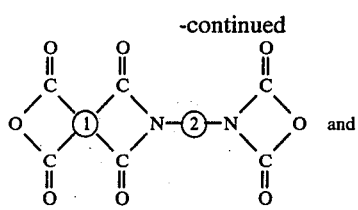

and

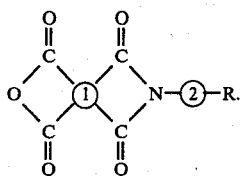

In each of the above classes I–IV,

and R are as defined above.

The imide anhydride curing agents of Class I of the invention may be prepared by reacting two moles of dianhydride per mole of the cycloaliphatic or aromatic $H_2N$—②—$NH_2$. Class II compounds may be prepared by reacting one mole of the diamine $H_2N$—②—$NH_2$ with one mole of dianhydride and one mole of

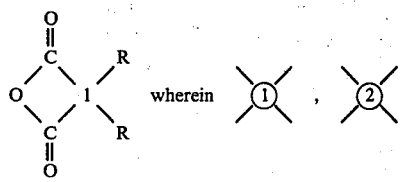

R is defined above. Class III compounds may be prepared by protecting one of amino groups of the $H_2N$—②—$NH_2$ with a suitable protecting group such as with a t-butylcarbonyl group or a benzylcarbonyl group. One mole of the protected amine is then reacted with one mole of the dianhydride and the protected amine deprotected using standard deprotecting techniques and deprotecting agents. Reaction of the deprotected amine derivative with phosgene followed by reaction with

HC—OH under cyclization conditions provides the Class III compound. Class IV compounds are prepared by reacting one mole of the dianhydride with one mole of the monoamine, R—②—$NH_2$, wherein R is as hereinbefore defined.

Illustrative of suitable dianhydrides for use in the preparation of the imide anhydride curing agents are:

cyclobutane tetracarboxylic anhydride,
benzene-1,2,4,5-tetracarboxylic anhydride,
cyclopentane-1,2,3,5-tetracarboxylic anhydride,
3,6-dimethylbenzene-1,2,4,5-tetracarboxylic anhydride,
3-methylcyclopentane-1,2,4,5-tetracarboxylic anhydride,
3-chlorobenzene-1,2,4,5-tetracarboxylic anhydride,
3-ethylbenzene-1,2,4,5-tetracarboxylic anhydride,
3-aminobenzene-1,2,4,5-tetracarboxylic anhydride,
3-amino-6-methylbenzene-1,2,4,5-tetracarboxylic anhydride,
6-hydroxybenzene-1,2,4,5-tetracarboxylic anhydride, and
3-benzenecarboxylic acid-1,2,4,5-tetracarboxylic anhydride.

Examples of amines that can be used in the preparation of the imide anhydrides of the invention are:

1,3-cyclobutane diamine,
2-chloro-1,3-cyclobutane diamine,
2-methyl-1,3-cyclobutane diamine,
2,4-dimethyl-1,3-cyclobutane diamine,
2-ethyl-1,3-cyclobutane diamine,
2-amino-1,3-cyclobutane diamine,
2-hydroxy-1,3-cyclobutane diamine,
2,4-dihydroxy-1,3-cyclobutane diamine,
2-carboxylic acid-1,3-cyclobutane diamine,
1,2-cyclobutane diamine,
2-chloro-1,2-cyclobutane diamine,
2-methyl-1,2-cyclobutane diamine,
2,4-dimethyl-1,2-cyclobutane diamine,
2-ethyl-1,2-cyclobutane diamine,
2-amino-1,2-cyclobutane diamine,
2-hydroxy-1,2-cyclobutane diamine,
2,4-dihydroxy-1,2-cyclobutane diamine,
2-carboxylic acid-1,2-cyclobutane diamine,
p-phenylene diamine,
2-chloro-1,4-phenylene diamine,
2-methyl-1,4-phenylene diamine,
2,4-dimethyl-1,4-phenylene diamine,
2-ethyl-1,4-phenylene diamine,
2-amino-4-phenylene diamine,
2-hydroxy-1,4-phenylene diamine,
2,4-dihydroxy-1,4-phenylene diamine,
2-carboxylic acid-1,4-phenylene diamine,
1,5-phenylene diamine,
2-methyl-1,5-phenylene diamine,
2,3-dimethyl-1,5-phenylene diamine,
2,3,4-trimethyl-1,5-phenylene diamine,
2,3,4,6-tetramethyl-phenylene diamine,
2-ethyl-1,5-phenylene diamine,
2-amino-1,5-phenylene diamine,
2-hydroxy-1,5-phenylene diamine,
2,4-dihydroxy-1,5-phenylene diamine,
2-carboxylic acid-1,5-phenylene diamine,
1,2,5-phenylene tetraamine,
2-hydroxy-1,5-phenylene diamine,
2,3-dihydroxy-1,5-phenylene diamine,
2,3,4-trihydroxy-1,5-phenylene diamine,
1,4-cyclohexane diamine,
2-methyl-1,4-cyclohexane diamine,
2,3-dimethyl-1,4-cyclohexane diamine,
2,3,5-trimethyl-1,4-cyclohexane diamine,
2,3,5,6-tetramethyl-1,4-cyclohexane diamine,
2-ethyl-1,4-cyclohexane diamine,
2-hydroxy-1,4-cyclohexane diamine,
2,4-dihydroxy-1,4-cyclohexane diamine,
2-carboxylic acid-1,4-cyclohexane diamine,
1,2,5-cyclohexane triamine,
1,2,3,5-cyclohexane tetramine,
2-hydroxy-1,4-cyclohexane diamine,
2,3-dihydroxy-1,4-cyclohexane diamine,
2,3,4-trihydroxy-1,5-cyclohexane diamine,
2,3,4,6-tetrahydroxyl-1,5-phenylene diamine, 1,2-cyclopentane diamine,
3-methyl-1,2-cyclopentane diamine,
3-hydroxy-1,2-cyclopentane diamine,
3-ethyl-1,2-cyclopentane diamine,
3-amino-1,2-cyclopentane diamine,
3-carboxylic acid-1,2-cyclopentane diamine,
3,4-dimethyl-1,2-cyclopentane diamine,
3,4-dihydroxyl-1,2-cyclopentane diamine,
1,4-pentane diamine,
3-methyl-1,4-cyclopentane diamine,
3-hydroxy-1,4-cyclopentane diamine,
3-ethyl-1,4-cyclopentane diamine,
3-amino-1,4-cyclopentane diamine,
3-carboxylic acid-1,4-cyclopentane diamine,
2,3-dimethyl-1,4-cyclopentane diamine,
2,3-dihydroxy-1,4-cyclopentane diamine,
3,4,5-trihydroxy-1,2-cyclopentane diamine,
2,3,5-trihydroxy-1,4-cyclopentane diamine,
3,4,5-trimethyl-1,2-cyclopentane diamine,
2,3,5-trimethyl-1,4-cyclopentane diamine,
aminocyclobutane,
2-methyl-3-aminocyclobutane,
2,4-dimethyl-1-aminocyclobutane,
3,4-dimethyl-1-aminocyclobutane,
2-hydroxy-3-aminocyclobutane,
2-chloro-3-aminocyclobutane monoamine,
2,4-dihydroxyl-1-aminocyclobutane,
aminobenzene,
3-methyl-1-aminobenzene,
3,5-dimethyl-1-aminobenzene,
2,3,4-trimethyl-1-aminobenzene
2,3,4,5-tetramethyl-1-aminobenzene
3-chloro-1-aminobenzene,
3-ethyl-1-aminobenzene,
1,3-diaminobenzene,
3-hydroxy-1-aminobenzene,
2-methyl-3-aminocyclohexane,
2,4-dimethyl-3-aminocyclohexane,
3,4-dimethyl-1-aminocyclohexane,
2-hydroxy-3-aminocyclohexane,
2-hydroxy-3-aminocyclohexane,
2-chloro-3-aminocyclohexane,
2,3,4-trimethyl-1-aminocyclohexane,
3-methyl-1-aminopentane,
3,4-dimethyl-1-aminopentane,
3,4,5-trimethyl-1-aminopentane,
2-methyl-1-aminopentane,
2,3-dimethyl-1-aminopentane,
3-hydroxy-1-aminopentane,
1,3-diaminopentane and
3-ethyl-1-aminopentane.

The expressions epoxy resins and polyepoxides are used herein interchangeably to refer to the broad class of epoxy-containing reactants which react with the imide anhydride curing agents to produce a hard infusible resin product. The polyepoxide can be a single compound containing at least two epoxy groups in which case it is a diepoxide. It can also contain a variety of molecular species having a varying number of epoxy groups per molecule such that the average number of epoxy groups per molecule, that is the epoxy equivalent value, is specified. The epoxy equivalent value of these polyepoxides comprising a mixture of molecular species is greater than one and is preferably about two or more, but will generally not be a whole integer. The epoxy equivalent value is obtained by dividing the average molecular weight of the polyepoxide by its epoxide equivalent weight (grams of the polyepoxide containing one gram equivalent of epoxide). The polyepoxide can be aliphatic, cycloaliphatic, aromatic, heterocyclic mixtures of these, saturated or unsaturated, and the like. It can be liquid or solid but must be soluble in the resin solution, or if not soluble capable of forming a homogeneous dispersion in the resin solution.

This broad class of epoxy resins which is useful in forming the epoxy-containing polymer with this resin-forming solution is exemplified by reference to several of the better known types. The glycidyl group of epoxy resins is an important and useful type of epoxy resin. This group includes the glycidyl ethers, the glycidyl esters, the glycidyl amines, and the like. The glycidyl ethers include the glycidyl ethers of mononuclear polyhydric phenols, polynuclear polyhydric phenols and the aliphatic polyols. They may be single compounds or more commonly are a mixture of compounds, some of which are polymeric in nature. Illustrative of glycidyl ethers are the di- or polyglycidyl ethers of ethylene glycol; trimethylene glycol; glycerol; diglycerol; erythritol; mannitol; sorbitol; polyallyl alcohol; butanediol; hydrogenated bisphenol A; and the like.

The glycidyl ethers of polyhydric phenols include the glycidyl ethers of resorcinol; hydroquinone; catechol; pyrogallol; and the like as well as the glycidyl ethers of polynuclear phenols such as bisphenol A; bis(4-hydroxyphenyl) methane, and the like, and glycidyl ethers of the novolac resins such as bisphenol F and the like. The epoxy resins also include epoxidized olefins generally based on naturally occurring oils, such as epoxidized soybean oil, epoxidized cotton seed oil, epoxidized castor oil, epoxidized linseed oil, epoxidized menhaden oil, epoxidized lard oil and the like, but also including epoxidized butadiene, epoxidized polybutadiene, and the like.

Preferred epoxy resins for use in the invention are polyglycidyl derivatives of aminophenols having the formula:

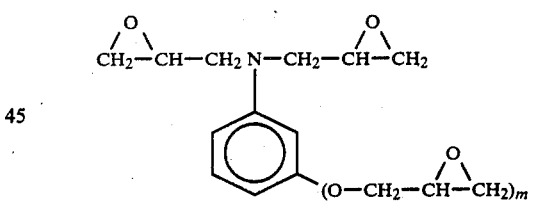

wherein m is 1 to 2. The preferred polyglycidyl derivative of aminophenol at the present time is triglycidyl p-aminophenol (m is 1). The polyglycidyl derivatives of aminophenols are normally fluid, viscous materials which are commercially available. Such polyglycidyl aminophenols can be prepared according to the disclosure of Reinking et al. U.S. Pat. No. 2,951,825.

If desired, other co-curing agents can be joined together with the imide anhydride component of the invention. Such co-curing agents, include for instance, anhydrides such as maleic anhydride, succinic anhydride, phthalic anhydride, tetrahydrophthalic anhydride, NADIC methyl anhydride, pyromellitic anhydride, and the like.

In forming the compositions of the present invention, the imide anhydride and epoxy resin components will be used in amounts sufficient to provide an effective weight ration A/E of anhydride:epoxy resin in the range of about 0.2–1.3:1.

When mixed anhydride curing systems are employed, it is preferred that at least about 40 percent of the total anhydride equivalents be provided by the imide anhydride component of the mixed anhydride curing systems. In like manner, when mixed epoxy resin systems are employed, it is preferred that at least about 40 percent of the total anhydride equivalents be provided by the imide anhydride component of the mixed anhydride curing systems. In like manner, when mixed epoxy resin systems are employed, it is preferred that at least 50 percent of the total epoxy equivalents be a polyglycidyl aminophenol component of such mixed epoxy resin compositions. Since solubilization of the imide anhydride in the epoxide component is a function of a number of variables, including particle size, amount of total imide anhydride and/or total epoxy resin, relative amounts of individual anhydride and/or individual epoxy resin, inter alia, some amount of routine experimentation may be required to obtain optimal compositions.

Because the epoxy resin systems of this invention are reactive at room temperature, mixing of the imide anhydride and the epoxy components will preferentially be accomplished at the job site. The reactive system is readily prepared by blending the curing agent system comprising imide anhydride preferably having a particle size below about 150 microns average diameter, into the epoxy resin system. In this regard, when mixed anhydride systems are employed, the individual anhydrides are preferably admixed prior to incorporation into the epoxy resin system, which itself can be a priorly admixed system comprising two or more epoxy resins. When employing mixed epoxy resin systems, the imide anhydride component can optionally, but less preferentially be mixed into one epoxy resin prior to being blended into the other epoxy resin or resins employed. Simple mixing means such as by stirring, ball milling and the like, is effective to cause substantial solubilization of the imide anhydride in the epoxy resin component. Prior to admixing of the imide anhydride and epoxy components, it can be advantageous to subject at least the imide anhydride to high shear forces, such as a three-roll mill, to reduce the average particle size, to enhance solubilization of imide anhydride particles. While mixing is preferably accomplished at room temperature, gentle heating of the imide anhydride/epoxy blend to temperatures below about 50° C. can be employed to abet solubilization, particularly at higher anhydride:epoxy ratios and when using mixed anhydride and/or mixed epoxy resin systems, without causing significant premature gellation of the blend. The blending of the imide anhydride and epoxy resin results in a mild, rapid endotherm on the order of 7°-12° C., followed by a gradual return to ambient temperature.

As aforementioned, because the epoxy resin compositions of the present invention are curable at room temperature, the compositions of this invention are preferably provided as a two-part system, one part comprising the imide anhydride and other curing agents when employed, together with conventional additives which are not reactive with the curing agents; and the other part comprising epoxide, together with conventional additives which are not reactive with epoxy resins. The individual parts are admixed at the job site and application is accomplished using the same techniques and equipment generally utilized with epoxy resin compositions. Even though curable at room temperatures, the compositions of this invention nevertheless remain workable for periods in excess of 8 hours before crosslinking has advanced to a degree sufficient to inhibit continued use of the blended compositions. Curing of the compositions can be effected at room temperature but curing at elevated temperatures below about 150° can be beneficial with respect to ultimate properties and setting times, depending upon the application. Curing at temperatures above 150° does not appear to provide any appreciable improvement in cured resin properties.

The following examples will serve to illustrate the invention. Unless otherwise noted, all amounts are in parts by weight.

EXAMPLE I

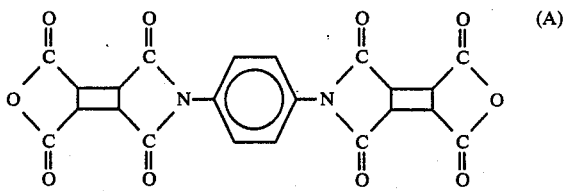

Cyclobutane tetracarboxylicdianhydride (CBTCDA) is reacted with para-phenylenediamine (PPDA) in a mole ratio of 2:1 according to the following procedure:

A solution of PPDA in dimethylformide (DMF) was introduced dropwise into a solution of CBTCDA at room temperature after four hours, a dark brown solid amide-acid precipitate is formed having the structure:

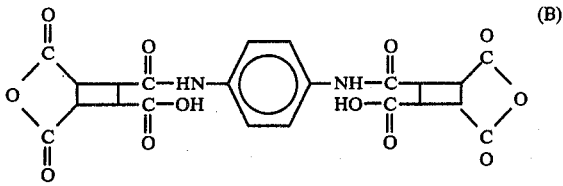

A mixture containing pyridine and acetic anhydride in a weight ratio of 3:2 is added to the amide-acid reaction product (B) and the temperature is raised to 80° C. The amide acid (B) is thus condensed to the imide anhydride (A). The imide anhydride (A) obtained is in solution and is separated by distilling off the solvents and drying in an air-circulated oven.

Alternately, the amide acid may be condensed to imide anhydride by temperature alone by heating above 180° C.

EXAMPLE II

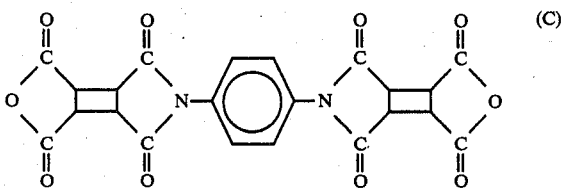

To synthesize imide anhydride (C) the procedure of Example I is repeated substituting meta-phenylenediamine for the paraphenylenediamine.

EXAMPLE III

Several epoxy resin/imide anhydride curing agent systems are prepared in the following manner:

Triglycidyl para-amino phenol (TGPAP) and imide anhydride identified in the Table below are ball milled together for 2 hours and then accelerator (benzyldimethylamine) 1 PHR is added and the mixture ball-milled for an additional 20 minutes. The anhydride to epoxide ratio is also shown in the Table below. The mixture is poured into a 5"×½"×½" mold and cured by heating two hours at 90° C. followed by 18 hours at 120° C. All of the imide anhydride curing agents successfully cured the epoxy resins system in the same manner as commercial anhydride curing agent and examination of the cured epoxy-imide systems under a polarizing like microscope shows a homogeneous one phase structure indicating complete solubility of the imide anhydride in the epoxy resin.

The thermal properties of the various epoxy-imide systems are reported in the Table below. In the determination of these properties the heat distortion temperature (HDT) of the cured epoxy-imide system is measured using a Plastic Deflection Tester (ASTM D648). In the test, 5"×½"×½" samples and a stress of 264 psi are used, and the glass transition (Tg) and the decomposition (Td) temperature of the epoxy-imide is measured using the DuPont 900 Differential Thermal Analyzer. The epoxy-imide anhydride system is found to exceed the limit of the Plastic Deflection Tester (260° C.).

TABLE

| # | Imide-Anhydride of | Anhydride Epoxy (A/E) | Heat Distortion Temp. HDT (°C.) | Glass Transition Temp. Tg (°C.) | Decomposition Td (°C.) |
|---|---|---|---|---|---|
| 1. | Example I (PPD-CBTCDA) | 0.27 | — | 128* | 304 |
|   |   | 1.00 | >260** | 146* | 305 |
| 2. | Example II (MPD-CBTCDA) | 0.27 | 74 | 90 | 305 |

Note:
*No real Tg is observed on the TMA thermogram. However, a small change in slope indicates a probable secondary Tg at temperature listed.
**The HDT of the sample exceeded the maximum temperature limited of the Plastic Deflection Tester.

The data of the Table show that the initial decomposition of the various epoxy-imide compositions studied is stable. The best heat distortion and glass transition temperatures is exhibited by the systems of the Example I. In the case of the Example I imide-anhydride/triglycidyl p-aminophenol, the heat distortion temperature is found to exceed the limit of the Plastic Deflection Tested (>260° C.).

The mechanical properties of the various epoxy-imide systems are found to be excellent as shown by tensile modules, tensile strength and impact strength determinations.

The imide anhydride/epoxy resin compositions of this invention can be used in adhesive, casting, molding, potting and encapsulation, coating, laminating, reinforced plastic, and the like applications to afford ultimate products having useful high temperature properties. The base epoxy resin compositions can also be used to modify, or can be modified by other epoxy resin systems; and other liquid and/or solid anhydrides can be employed as cocuring agents. The base epoxy resin compositions can be modified also by the incorporation of other resinous film forming material, such as polybutadiene, hydroxy- and carboxy-functional polybutadiene, polyamides, and the like to improve flexibility, impact resistance, etc. There may be incorporated into the compositions of the invention, whether or not modified, those additives conventionally employed with epoxy resin compositions including, without limitation thereto, solvents, fillers, particularly metal and conductive metallic fillers, plasticizers, flexibilizers, reinforcing fibers, carboxylic acids, inorganic acids, free radical sources, coupling agents such as polyfunctional organosilanes and the like, antioxidants, catalysts, and the like.

The other epoxy resins which can be combined with the base epoxy resin compositions of the invention can be broadly described as organic materials having a plurality of reactive 1,2-epoxy groups. Such epoxy materials can be monomeric or polymeric, saturated or unsaturated, aliphatic, cycloaliphatic, aromatic or heterocyclic, and they may be substituted if desired with substituents other than epoxy groups, such as hydroxyl groups, either radicals, halogen atoms, and the like. Representative epoxy materials include, without limitation thereto, epoxy polyethers obtained by reacting an epihalohydrin with a polyhydric phenol or a polyhydric alcohol; polyepoxy-polyhydroxyethers obtained by reacting a polyepoxide with a polyhydric phenol or a polyhydric alcohol; epoxy novolaks; and the like. Further details of epoxy co-reactants which can be employed according to the present invention can be found in U.S. Pat. Nos. 2,633,548; 2,872,427; 2,884,408; and 3,759,914, among others.

We claim:
1. A room temperature-stable two-pack epoxy resin system consisting essentially of
(a) a first pack comprising at least one imide-anhydride having the structure

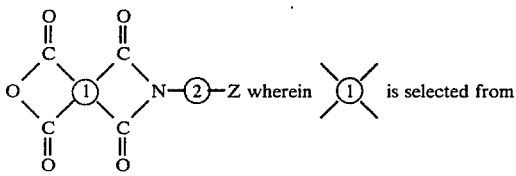

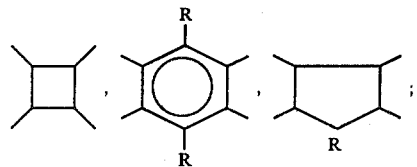

—②— is selected from

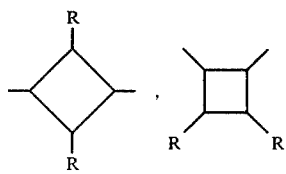

-continued

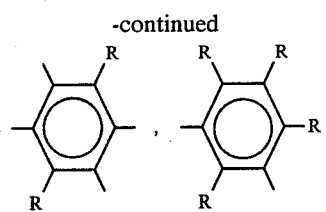

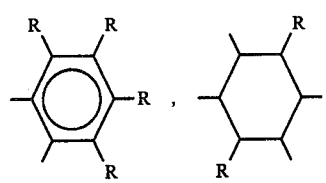

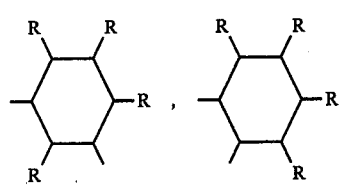

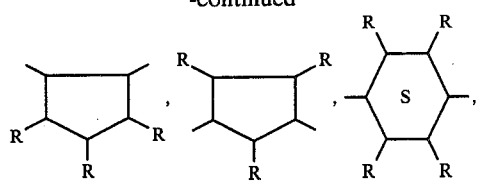

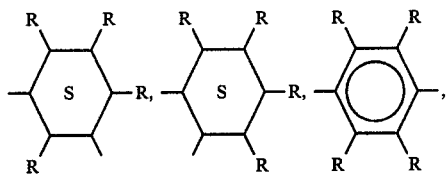

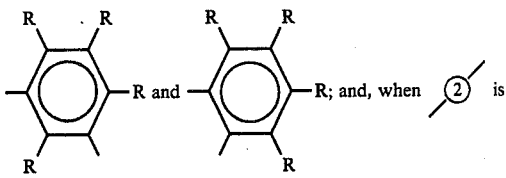

Z is selected from

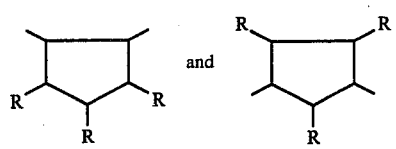

wherein R is selected from the group consisting of hydrogen, halogen, alkyl group having from 1 to 4 carbon atoms, hydroxyl, carboxyl and amine; with the proviso that, in all cases, either

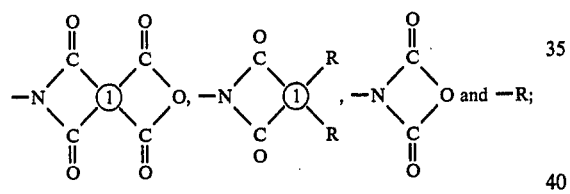

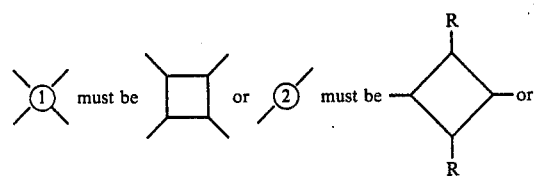

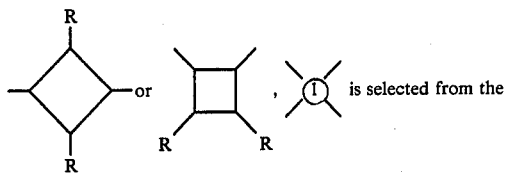

group consisting of 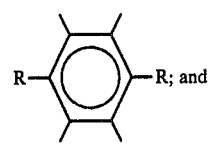

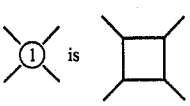

(b) a second pack comprising an epoxy resin substantially free of active hydrogen having a 1,2 epoxy equivalent value of greater than 1 and capable of solubilizing said imide anhydride.

2. An epoxy resin system according to claim 1 wherein

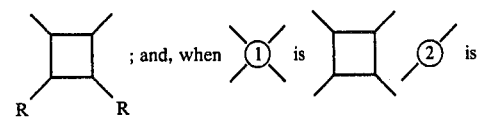

3. An epoxy resin system according to claim 2 wherein Z is

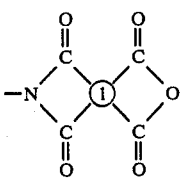

4. An epoxy resin system according to claim 3 wherein

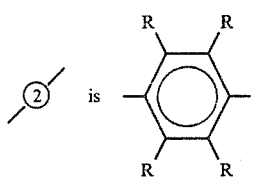

5. An epoxy resin system according to claim 3 wherein

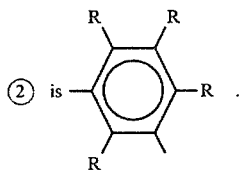

6. An epoxy resin system according to claim 1 wherein the epoxy resin comprises at least one polyglycidyl aminophemol having the structure

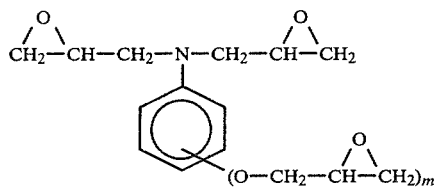

wherein m is 1 or 2.

7. An epoxy resin system according to claim 6 wherein

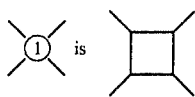

8. An epoxy resin system according to claim 7 wherein Z is

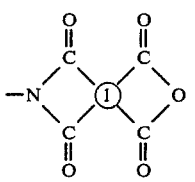

9. An epoxy resin system according to claim 8 wherein

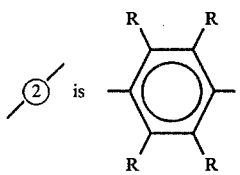

10. An epoxy resin system according to claim 8 wherein

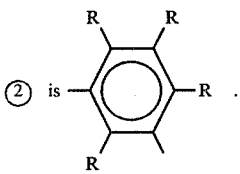

* * * * *